(12) United States Patent
Lindgren et al.

(10) Patent No.: US 11,173,228 B2
(45) Date of Patent: Nov. 16, 2021

(54) MEDICAL DRESSING COMPRISING A CARRIER AND A COMPOSITE MATERIAL

(71) Applicant: Mölnlycke Health Care AB, Gothenburg (SE)

(72) Inventors: Lars Lindgren, Gothenburg (SE); Marina Craig, Åsa (SE); Simon Hjelm Jonasson, Luleå (SE); Romain Bordes, Mölndal (SE); Eric Wellner, Gothenburg (SE)

(73) Assignee: Mölnlycke Health Care AB, Gothenburg (SE)

( * ) Notice: Subject to any disclaimer, the term of this patent is extended or adjusted under 35 U.S.C. 154(b) by 288 days.

(21) Appl. No.: 16/311,300

(22) PCT Filed: Jul. 7, 2017

(86) PCT No.: PCT/EP2017/067112
§ 371 (c)(1),
(2) Date: Dec. 19, 2018

(87) PCT Pub. No.: WO2018/007595
PCT Pub. Date: Jan. 11, 2018

(65) Prior Publication Data
US 2019/0192730 A1    Jun. 27, 2019

(30) Foreign Application Priority Data
Jul. 8, 2016 (EP) .................... 16178578

(51) Int. Cl.
*A61F 13/00* (2006.01)
*A61L 15/34* (2006.01)
(Continued)

(52) U.S. Cl.
CPC .......... *A61L 26/0095* (2013.01); *A61L 15/26* (2013.01); *A61L 15/28* (2013.01); *A61L 15/34* (2013.01);
(Continued)

(58) Field of Classification Search
None
See application file for complete search history.

(56) References Cited

U.S. PATENT DOCUMENTS

| 5,266,330 | A | 11/1993 | Cannon |
| 6,284,941 | B1 * | 9/2001 | Cox .................... A61K 9/7084 602/41 |

(Continued)

FOREIGN PATENT DOCUMENTS

| CN | 104918589 A | 9/2015 |
| WO | WO-96/36315 A1 | 11/1996 |

(Continued)

OTHER PUBLICATIONS

Hu, Z. et al., Dried and Redispersible Cellulose Nanocrystal Pickering Emulsions. ACS Macro Lett. 2016; 5(2):185-9.
(Continued)

*Primary Examiner* — Kim M Lewis
(74) *Attorney, Agent, or Firm* — Ballard Spahr LLP

(57) ABSTRACT

Disclosed is a medical dressing having a carrier material and a composite material. The composite material includes oil droplets dispersed in a matrix. The matrix includes one or more cellulose derivatives and nanocellulose.

18 Claims, 6 Drawing Sheets

(51) Int. Cl.
*A61L 26/00* (2006.01)
*A61L 15/28* (2006.01)
*A61L 15/26* (2006.01)
*A61L 15/42* (2006.01)
*A61L 15/58* (2006.01)

(52) U.S. Cl.
CPC ............ *A61L 15/425* (2013.01); *A61L 15/58* (2013.01); *A61L 26/0023* (2013.01)

(56) References Cited

U.S. PATENT DOCUMENTS

| | | | | |
|---|---|---|---|---|
| 7,939,570 | B2* | 5/2011 | Raul | A61K 8/89 514/770 |
| 8,821,920 | B2* | 9/2014 | Muller | A61P 25/02 424/448 |
| 10,369,247 | B2* | 8/2019 | Fung | A61L 15/225 |
| 2008/0249453 | A1* | 10/2008 | Effing | A61K 33/38 602/48 |
| 2013/0150765 | A1* | 6/2013 | Moghe | A61F 13/00063 602/48 |
| 2015/0343748 | A1* | 12/2015 | Broyles | A61F 13/51401 428/220 |
| 2016/0369121 | A1* | 12/2016 | Lapidot | C05F 11/00 |
| 2020/0085720 | A1* | 3/2020 | Li | A61K 8/895 |

FOREIGN PATENT DOCUMENTS

| | | |
|---|---|---|
| WO | WO-2010/025224 A1 | 3/2010 |
| WO | WO 2014/113652 | 7/2014 |

OTHER PUBLICATIONS

M., Haritha et al., Dry Emulsion: A Promising Dosage Form to Deliver Lipophilic Drug Molecules with Improved Stability and Effectiveness. In J Res Pharm Biotechnol. 2013; 1(1):119-21.

International Search Report and Written Opinion dated Sep. 26, 2017 by the International Searching Authority for Patent Application No. PCT/EP2017/067112, which was filed on Jul. 7, 2017 and published as WO 2018/007595 on Jan. 11, 2018 (Inventor—Lingren et al., Applicant—Mölnlycke Health Care AB) (10 pages).

Gelling Fiber Dressing. 2015. Retrieved from the Internet: URL <http://www.molnlycke.co.uk/pagefiles/66712/exufiber product sheet.pdf> [retrieved Sep. 18, 2017].

* cited by examiner

MEDICAL DRESSING COMPRISING A CARRIER AND A COMPOSITE MATERIAL

CROSS-REFERENCE TO RELATED APPLICATIONS

This application is a U.S. National Phase Application of International Application No. PCT/EP2017/067112, filed Jul. 7, 2017, which claims priority to European Application No. 16178578.7, filed Jul. 8, 2016, each of which are hereby incorporated by reference in their entirety.

TECHNICAL FIELD

The present disclosure relates to a medical dressing. More specifically, the present disclosure relates to a medical dressing comprising a carrier and a composite material. Moreover, the present disclosure relates to a method of producing the medical dressing.

BACKGROUND OF THE INVENTION

Materials originating from emulsions is an area within material sciences which has gained increased popularity during the last decades, mainly due to the fact that the resulting materials exhibits interesting physical properties which are required, in for example drug-delivery systems and scaffolds for tissue engineering.

Polymers issued from renewable resources have also attracted considerable attention in the last two decades, predominantly due to their environmentally friendly properties, renewability, good biocompatibility, biodegradability, bioactivity, and modifiability.

Cellulose is a typical example which also exhibits a hierarchical structure of interest of various fields and applications as it combines fibers and polymeric species organized in a functional design.

Nanofibers prepared from the renewable polymers can combine the excellent properties of the renewable polymer and nanofiber, which attracts attention within various fields and applications.

A wound caused by an injury or disease, such as diabetic foot ulcer or venous leg ulcers, may be treated by the use of a medical dressing, such as a bandage or wound dressing, to promote healing by preventing infection and leakage from the wound. The wound may be subjected to severe bacterial colonization's and hence bacterial infections, and especially for chronic wounds, cavity wounds and burns, infections are very common and needs to be addressed.

The risk of infections may be reduced by the use of antimicrobial substances and thus creating a better outcome for the patient. Also, wound healing substances of all kinds are interesting for all types of wounds, as well as debridement and cleansing substances for wounds that either need wound treatment or surgical prevention treatment.

Medical dressings may also be used for pressure ulcer prevention by minimizing shear and friction, distributing pressure and ensuring a good microclimate. Protecting and monitoring the condition of the skin is also important for preventing pressure ulcer and topical application of skin protecting compositions and substances is also used for preventing the development of pressure ulcer.

However, applying soothing oils and other beneficial substances may be seen as cumbersome and messy and to provide medical dressings pre-prepared with active compositions may suffer from problems with stability of such active compositions, as the activity may be reduced and/or the compositions may oxidize over time, e.g. upon contact with air, thereby resulting in reduced functionality and shortened shelf-life.

There is therefore a need for a medical dressing which is easy and convenient to use which medical dressing avoids or minimizes at least one of the disadvantages discussed above.

SUMMARY OF THE INVENTION

One object of the present disclosure is to provide a medical dressing capable of releasing an oil composition, thus having improved pressure ulcer prevention and/or microbial functionality, which medical dressing does not suffer from the disadvantages outlined above, or at least minimizes the disadvantages.

These and other objects may be provided by a medical dressing according to the appended claims.

As such, and according to a first aspect, the present disclosure relates to a medical dressing having a first side adapted to face a wound or tissue site when in use and a second side, opposite to said first side. The medical dressing comprises a carrier material and a composite material. The composite material comprises oil droplets dispersed in a matrix. The matrix comprises one or more cellulose derivatives and nanocellulose.

The fact that the medical dressing comprises a composite material comprising oil droplets dispersed in a matrix as disclosed herein, provides a medical dressing which may retain and encapsulate a relatively large amount of oil and which also allows for oil leakage when pressure/shear force/or other force is applied to the medical dressing. The pressure exerted to the medical dressing breaks up the cell structure of the material and the oil is released to the site to which the medical dressing is applied. The oil protects and strengthens the skin at skin pressure points against pressure ulcers and thereby provides a pressure ulcer prevention effect to the patient. The composite material will also, in contact with wound exudates, redisperse into a liquid phase such that the oil comprised in the emulsion is released to the wound site.

As the composite material in the medical dressing according to the present disclosure is in a dry and solid form prior to and during application to a wound or tissue site, the application of the medical dressing will be facilitated as no smearing will occur when applying the medical dressing to the wound or tissue site. This may improve the positioning and comfort to the user. If a cover layer with an adhesive surface is used, semi-liquid substances may also impair the adhesion of the peripheral edge portion(s) of the cover layer to the skin, which may deteriorate the function and intergrity of the medical dressing. Also, storage of the medical dressing is improved by the fact that the composite material is dry prior to use, as no migration of the composite material within the medical dressing may occur during storage.

Furthermore, due to the low water content of the composite material, the risk for microbial growth is avoided without the need of including additional preservatives. Which may be beneficial for wound healing and which may maintain or even increase the intended shelf-life of the medical dressing, which normally is between 3-5 years.

It has thus been found that the composite material as disclosed herein is specifically advantageous for use in medical dressings as it provides a medical dressing which is easy and convenient to apply, has a long shelf-life and which does not require complex protecting packages.

The dispersed oil droplets may comprise one or more antimicrobial oil(s), such as for example cinnamaldehyde, eugenol, limonene, bay oil, thyme oil and/or clove oil and may reduce the infection risk at the wound site and thereby improve the wound healing.

By "medical dressing" herein is meant a pad, net, foam, fibrous structure, film, gel, or the like, applied to a wound to promote healing and/or prevent further harm, or alternatively, applied to the skin to prevent the formation of a wound, such as for pressure ulcer prevention.

By "composite material" herein is meant a structure made up of at least three distinct components; a matrix in the form of a solid and dry continuous phase comprising one or more cellulose derivative(s) and nanocellulose and an oil phase in the form of oil droplets dispersed in the matrix.

By "matrix" herein is meant a continuous phase wherein the oil droplets are dispersed.

The composite material is a so-called emulsion, or emulsion-templated, originating material. The emulsion is an oil-in-water (o/w) emulsion stabilized by nanocellulose and the water soluble cellulose derivative(s) in the continuous phase. The o/w emulsion is thus a pickering emulsion, i.e. stabilized by solid particles in the form of nanocellulose bound with a water-soluble polymer such as a cellulose derivative. The cellulose derivative(s) and the nanocellulose form a solid matrix upon drying, in which the oil remains dispersed. The composite material produced could also be referred to as a dry emulsion comprising a solid continuous phase and a dispersed oil phase in the form of oil droplets.

By "nanocellulose" herein is meant nano-structured cellulose, such as cellulose nanofibers (CNF) also called microfibrillated cellulose (MFC), nanocrystalline cellulose or bacterial nanocellulose, which refers to nano-structured cellulose produced by bacteria.

The term "cellulose nanofibers", refers to small diameter, high length-to-diameter ratio substructures. The free and individual fibres typically have a diameter of from 5 nm to 300 nm at all points along the fibre, preferably from 5 nm to 100 nm at all points along the fibre. The diameter of the fibers may be measured by means of Atomic Force Microscope (AFM), as disclosed under "Characterization of CNC" The cellulose nanofibers may exist as free and individual fibrils and/or as free clusters of such fibrils. Other available methods which may be used are Scanning Electron Microscope (SEM) and Transmission Electron Microscope (TEM).

By "wound site" herein is meant an open or closed (e.g. closed incision) wound or damage located on or within any tissue, such as dermal tissue, bone tissue, adipose tissue, muscle tissue, neural tissue, vascular tissue, connective tissue, cartilage, tendons, or ligaments.

By "tissue site" herein is meant areas of any tissue without an open wound. The tissue site may be damaged tissue, or areas of tissue which are not wounded or damaged. When the areas of tissue are not wounded or damaged, this may for example be areas in which promotion of the growth of tissue or stimulation of the tissue is needed.

The medical dressing may be used for pressure ulcer prevention.

The medical dressing may also be used for prevention of bacterial infection.

Optionally, the nanocellulose is present in an amount within the range of from 0.5 to 6% by weight of the total composite material, i.e. after drying. Optionally, the nanocellulose is present in an amount within the range of from 1 to 4% by weight of the total composite material.

The fact that the nanocellulose is present in an amount of at least 0.5% by weight, such as at least 1% by weight, or at least 1.5% by weight, ensures a stable emulsion.

Optionally, the one or more cellulose derivative(s) is/are present in an amount within the range of from 3 to 20% by weight of the total composite material. Optionally, the one or more cellulose derivative(s) is/are present in an amount within the range of from 3 to 10% by weight of the total composite material.

The fact that the one or more cellulose derivative(s) is/are present in an amount within the range of from 3 to 20% by weight of the total composite material provides stability to the emulsion and strength to the resulting composite material.

Optionally, oil is present in an amount within the range of from 74 to 96.5% by weight of the total composite material, such as from 84 to 96% by weight of the total composite material.

Optionally, the carrier material comprises a net, foam, a fibrous structure, a film, a gel, or a silicone based or acrylic adhesive, or any combinations thereof. In embodiments of the invention, the carrier material may comprise a polyamide net, a polyurethane foam, or a nonwoven. For example, in embodiments of the invention, the carrier material may comprise a hydrophilic polyurethane foam, a hydrophobic polyurethane foam, or a nonwoven comprising gel forming fibers. The carrier material may comprise hydrofibers. Such fibers may be beneficial due to their initial dry structure and their gel forming properties during use. A nonwoven structure comprising PVA fibers will have a structure efficiently holding the composite material and which does not absorb the composite material during use, maximizing the effect of the composite material.

A hydrofiber is a gelling fiber/and may for example comprise PVA fibers, such as Exufiber® from Mölnlycke Health Care, nonwoven sodium carboxymethylcellulose fibers or regenerated cellulose fibers.

In embodiments of the invention, the carrier material may comprise a nonwoven and/or foam layer wherein the carrier material further comprises absorbent particles or fibers, such as, for example, so-called superabsorbent particles or fibers.

Optionally, the composite material may be incorporated into the carrier material and the carrier material may be provided on the first side of the medical dressing and thereby form a wound or tissue contacting layer.

The fact that the carrier material is provided on the first side of the medical dressing allows rapid release of the oil, and/or the beneficial substances dissolved in the oil droplets, to the tissue site resulting in an improved and rapid effect. As the carrier material is dry and solid prior to use, the main part of the oil and/or substances comprised therein will be in direct contact with the tissue siteand the amount of composite material migrating upwards, away from the wound or tissue site, will be minimized.

The carrier material may have a a first side, adapted to face a wound or tissue site when in use and a second side, opposite to the first side, and the composite material may be provided in a higher concentration proximate to the first side of the carrier material than proximate to the second side of the carrier material. The carrier material may thereby have a gradient of the composite material from the first side to the second side, where the first side comprises a higher amount of composite material than the second side.

Incorporation of the composite material into the carrier material may be beneficial for manufacturing reasons. It may also allow the carrier material to preserve its structure, function and appearance, while adding the functionality of the composite material.

The medical dressing may, optionally, comprise a support layer and the carrier material having composite material incorporated therein may have a no-load thickness of from 0.1 to 10 mm.

The fact that the medical dressing further comprises a support layer enables the medical dressing to include additional functionalities into the dressings. It may be beneficial for manufacturing reasons as the carrier material may be kept relatively thin and thereby decrease the amount of composite material needed for a predetermined amount of composite material in contact with the wound or tissue site. As the carrier material is dry and solid prior to use, the main part of the oil and/or substances comprised therein will be in direct contact with the wound or tissue site and the amount of composite material migrating upwards, away from the wound or tissue site, and into the support layer will be minimized.

Optionally, the support layer may be a resilient layer, such as a foam layer or a film layer. Such medical dressing would, for example, be suitable for pressure ulcer prevention and wound care due to the resilience and bolterings effect of the material.

Optionally, the carrier material is a silicone based adhesive and the support layer is a foam layer or a film layer. The support layer may be a foam layer, such as an open-cell foam layer.

It has been found that silicone based adhesive provides an advantageous carrier due to its firm but yet resilient structure, allowing rapid release of composite material when exerted to pressure or wound exudate but still forming a protective structure against a pre-release of the composite material.

The composite material may form a, continuous or discontinuous, layer on the first, wound or tissue contacting, side of the carrier material.

The composite material may be applied by spray coating, print coating, slot dye coating impregnation, dipping or similar application methods.

Optionally, the medical dressing comprises a cover layer, provided at a second side of the medical dressing. A cover layer may cover and extend over the underlying, wound or tissue facing, layer(s) such that a cover layer border being adapted to adhere to the skin of a user is formed. In this way the underlying layer(s), such as the carrier material and possible support layer(s), are covered and held in placed when in use.

The medical dressing may furthermore be provided with a protecting release layer. Such release layer may protect both the adhesive layer provided on the cover layer border and also the carrier material and/or the composite material.

Optionally, the medical dressing comprises the composite material in an amount in the range of from 0.01 to 600 $g/m^2$ of the carrier material.

Optionally, if the composite material is coated/deposited onto or dispersed within a silicone based or acrylic adhesive, the carrier material in the form of a silicone based or acrylic adhesive may be combined with a secondary carrier, such as a net, a foam, a fibrous structure, a film or a gel. The amount of composite material may be in the range of from 5 to 30% wt of the silicone based or acrylic adhesive. The amount composite material may be in the range of from 0.01 to 60 $g/m^2$ of the medical dressing secondary carrier material.

Optionally, if the carrier material is a polyurethane foam, nonwoven, hydrofibre, etc., the amounts of added composite material may be higher than for use with an adhesive. The composite material may be provided in a higher amount, based on weight, proximate to the first, wound or tissue facing, side of the carrier material than proximate to the second side of the carrier material. The amount of the composite material may then be in the range of from 0.1 to 50 $g/m^2$ on the first side. The carrier material may thereby have a gradient of the composite material from the first side to the second side, where the first side comprises a higher amount of composite material than the second side. If both sides are impregnated, the amount of composite material may be in the range from 0.1 to 100 $g/m^2$ when both sides are impregnated. The material could also be entirely soaked in the emulsion, such as providing an amount in the range of from 1 to 600 $g/m^2$.

As an example, a polyurethane foam may comprise up to about 400%, based on the total weight, of the composite material. The foam may for example be impregnated by dipping the foam in a redispersed composite material, thus being in a liquid phase, before allowing the composite material to dry in the foam structure.

The fact that the carrier materials may comprise such high amounts of composite material allows a relatively high amount of oil or substance comprised in the oil phase to be released to the wound or tissue site if desired. The amount may however naturally be regulated to lower levels by lowering the content in the oil phase or by adding less composite material to the carrier material.

In a second aspect, the present disclosure relates to a medical dressing comprising a carrier material in the form of a gel, such as a hydrogel or a hydrofiber. The gel comprises an oil-in-water emulsion comprising oil droplets dispersed in an aqueous phase comprising a matrix. The matrix comprises one or more cellulose derivative(s) and nanocellulose.

A hydrogel is a cross-linked polymer gel. Hydrogels are typically very flexible. Hydrogels provide and maintain a moist environment at the contact point on skin by increasing moisture content. Generally, hydrogels can be removed without trauma to the wound. Common ingredients are for example polyvinyl alcohol, sodium polyacrylate, acrylate polymers and copolymers with hydrophilic groups. Commercially available examples of a hydrogel are Flexigel Hydrogel Sheet available from Smith & Nephew, Tegaderm CHG dressing available from 3M Company, St. Paul, Minn.

The fact that the medical dressing comprises a gel and an oil-in-water (o/w) pickering emulsion as disclosed herein provides a medical dressing which may retain and encapsulate a relatively large amount of oil and wherein the gel together with the oil can enable superior wound debridement. A medical dressing comprising a gel, such as a hydrogel or a hydrofiber, may furthermore provide a number of properties and/or functions which may be advantageous to treat or prevent a wound including, inter alia, shielding the skin or wound against mechanical stress, carrying a high amount of emulsion and provide pain relief at the wound site or at a pressure point.

The carrier material in the form of a gel may have a first side, adapted to face a wound or tissue site during use, and a second side, opposite to said first side. The oil-in-water emulsion may be provided in a higher concentration proximate to the first side of the gel than to the second side of the gel. The gel may thereby have a gradient of the oil-in-water emulsion from the first side to the second side, where the first side comprises a higher concentration of oil-in-water emulsion than the second side. The gradient may be a linear or a step-wise gradient.

The gel may comprise the o/w emulsion in an amount ranging from 0.1 to 30 wt. % of the gel.

The matrix comprising one or more cellulose derivative(s) and nanocellulose may be enriched by the nanocellulose and/or the one or more cellulose derivative(s) at the interface between each of the oil droplets and the matrix such that encapsulation of said oil droplets is provided.

Each of the oil droplets may thus be encapsulated by the one or more cellulose derivative(s) and/or by the nanocellulose.

The matrix may be enriched by the nanocellulose at the interface between each of the oil droplets and the matrix such that each of the oil droplets is encapsulated in nanocellulose.

The matrix may also be enriched by the one or more cellulose derivative(s) at the interface between each of the oil droplets and the matrix such that each of the oil droplets is encapsulated in one or more cellulose derivative(s).

The enrichment on the interface between the matrix and each of the oil droplets, in the composite material or in the o/w emulsion, may be provided by the one component of the one or more cellulose derivative(s) or the nanocellulose that is the more surface active component in the o/w emulsion. The most surface active component may be enriched on the interface between the oil droplets and the matrix, while the least surface active component may stabilize the system around the encapsulated oil droplet. It is however the synergistic interactions between the one or more cellulose derivative(s) and the nanocellulose that creates the stable and resilient composite material.

By "enriched" herein is meant an increase in amount and density. Hence, the one or more cellulose derivative(s) and/or the nanocellulose is/are increased in amount and density, as compared with the amount and density of the matrix, at the interface between each of the oil droplets and the matrix to such an extent that an encapsulation, i.e. complete coverage, of each of the oil droplets in the matrix is provided.

By "interface" between each of the oil droplets and the matrix is meant the surface forming the common boundary between the oil droplets and the matrix.

Examples when the nanocellulose may be enriched at the interface between the oil droplets and the matrix and thus encapsulates the oil droplets are when the matrix comprises HEC and/or CMC as cellulose derivative(s) and the nanocellulose is cellulose nanocrystals.

Examples when the one or more cellulose derivative(s) may be enriched at the interface between the oil droplets and the matrix and thus encapsulates the oil droplets are when the matrix comprises cellulose nanocrystals and the one or more cellulose derivative(s) is HPMC or HMPC and EHEC in combination.

Optionally, the nanocellulose is cellulose nanocrystals.

The term "cellulose nanocrystals", or "CNC", as used herein, refers to shorter fibers having a length within the range of from 30 to 1000 nm. The width of the cellulose nanocrystals normally is within the range of from 3 to 50 nm. CNCs are generally prepared by subjecting native fibers to controlled acid hydrolysis that cleaves the glycosidic bonds of cellulose in the disordered (or amorphous) regions of microfibrils, leaving crystalline segments intact. For CNCs isolated from Microcrystalline Cellulose (MCC) length and width ranges from 30 to 300 nm and from 3 to 50 respectively, whereas crystals isolated from cotton have a length within the range of from 70 to 300 nm and a width within the range of from 5 to 15 nm. The cellulose nanocrystals referred to herein is cellulose nanocrystals purified from cellulose or from cotton. One acid which may be used in to isolate the CNCs is sulphuric acid. The length of the fibers may be measured by means of Atomic Force Microscope (AFM), as disclosed under "Characterization of CNC".

The fact that the oil droplets are provided in a matrix comprising one or more cellulose derivative(s) and nanocellulose, such as cellulose nanocrystals, provides a reduced standard deviation between the oil droplet radii and a highly stable dry emulsion/composite material. This is believed to be due to the short length of the nanocellulose, which provides good functionality as emulsion stabilizer and to a synergistic effect due to interactions between the cellulose derivative(s) and the nanocellulose, such as cellulose nanocrystals.

Generally, a suitable o/w emulsion is formed according to the disclosure herein by firstly dissolving at least one polymeric cellulose derivative (referred to herein as "cellulose derivative", such as HPMC) in an aqueous phase.

Optionally, one or more cellulose derivative(s) is/are cellulose ether derivative(s), and optionally, the one or more cellulose ether derivative(s) is/are selected from the group consisting of hydroxypropylmethyl cellulose (HPMC), carboxymethyl cellulose (CMC), hydroxyethyl cellulose (HEC), ethylhydroxyethyl cellulose (EHEC), and any combinations thereof.

Optionally, the one or more cellulose derivative(s) is/are selected from hydroxypropylmethyl cellulose (HPMC) and hydroxyethyl cellulose (HEC) or carboxymethyl cellulose (CMC).

In some alternative aspects, alternative water-soluble polymers may be used instead of a polymeric cellulose derivative. Suitable alternative water soluble polymers include synthetic polymers as well as those derived from natural materials. One example of a suitable alternative water soluble polymer is polyvinyl alcohol, PVA. Suitable properties of such alternative polymers may be those described below for cellulose derivatives Optionally, the oil droplets comprise oil selected from the group consisting of paraffin oil e.g. ondina oil, corn oil, silicone oil, canola oil, cinnamaldehyde oil, eugenol, limonene, tea tree oil, coconut oil, olive oil, sunflower seed oil, ginger oil, orange oil, lemon oil, pine oil, bay oil, thyme oil, clove oil and cinnamon bark oil.

Optionally, the matrix comprises a divalent cation. Optionally, the matrix comprises a divalent cation selected from $Ca^{2+}$, $Mg^{2+}$, $Mn^{2+}$ and $Zn^{2+}$. The matrix may optionally comprise a beneficial substance being both hydrophilic and comprising charges instead of the salts.

Optionally, the divalent cation is provided in an amount of 0.1 M of the composite material.

Optionally, the divalent cation is provided in an amount of at least 0.05 Molar of the oil-in-water emulsion, such as from 0.05-2.0 Molar. The divalent cation may for example be added to the oil-in-water emulsion in the form of $CaCl_2$.

The provision of a divalent cation reduces electrostatic repulsion between the nanocellulose and thereby increases the stability of the emulsion.

Optionally, the oil droplets further comprises hydrophobic, oil soluble substances such as vitamin D, vitamin E, hydrophobic antimicrobial substance(s), surfactants, oil soluble iodide complexes, oil soluble iodide molecules, antibiotics, coumarin and/or phenolic compounds.

Examples of suitable hydrophobic antimicrobial substance are cetrimonium stearate and other hydrophobic quaternary ammonium compounds (QACs). Examples of suitable surfactants are Oleyl alcohol and ethoxylated fatty alcohols. An example of a suitable phenolic compound is 2-hydroxybenzoic acid. Additionally, excipients may be included to increase the solubility of substances which may otherwise be difficult to dissolve.

By "hydrophobic substance" herein is meant substances that are insoluble or poorly soluble in water, such that the water solubility 5 g/l or less, such as 1 g/l or less.

By "oil-soluble substance" is meant substances that are soluble in oil, for example, substances comprising hydrophobic components, such as surfactants.

Normally, the oxidization of active compositions is a problem, since the active agents risk losing their activity after oxygen exposure and thus gives the medical dressing comprising such substances a poor shelf life. Further, active agents in a dressing may also react, bind or otherwise interact with materials of the dressing resulting in reduced activity thereof. Although hydrophobic active agent(s) may be mixed with an oil and provided directly to a medical dressing and thus be protected to some extent, the oil may however be oxidized and/or the active agents may eventually emerge to the surface of the oil and thus be exposed to oxidation. In a medical dressing according to the present disclosure, these problems may be avoided or at least minimized as active agents, e.g. the hydrophobic active agent(s), may be mixed into the oil which is dispersed in the matrix of the composite material and thereby protected from the surrounding environment, e.g. reduced oxygen exposure and contact with dressing material.

The medical dressing according to the present disclosure thus avoids oxidation of the oil and the active agent if present, and the pressure triggered release allows for a medical dressing for use in pressure ulcer prevention that releases nurturing oils and/or active skin strengthen agents upon pressure, e.g. vitamin D, vitamin E, antifungal agents, etc.

Optionally, the medical dressing may be used in pressure ulcer prevention.

A third aspect of the present disclosure relates to a method of producing a combined carrier material and composite material for use as a component in the medical dressing according to a first aspect herein, comprising the steps of;
a) providing an oil-in water emulsion comprising or consisting of oil droplets dispersed in an aqueous phase comprising one or more cellulose derivatives and nanocellulose;
b) contacting a carrier material with the oil-in-water emulsion; and
c) drying the oil-in-water emulsion until 50-100% by weight of the water comprised in the oil-in-water emulsion has evaporated, before or after step b).

Optionally, the oil-in-water emulsion is dried until 100% by weight of the water comprised in the oil-in-water emulsion has evaporated, thereby providing the composite material.

Optionally, the carrier material comprises a net, a foam, a fibrous structure, a film, a gel, a silicone based adhesive or an acrylic adhesive, or any combinations thereof.

A fourth aspect of the present disclosure relates to a method of producing a carrier material in the form of a gel, such as a hydrogel or a hydrofiber, comprising an oil-in-water emulsion for use as a component in the medical dressing according to a second aspect herein, comprising the steps of;
a) providing an oil-in water emulsion comprising or consisting of oil droplets dispersed in an aqueous phase comprising one or more cellulose derivatives and nanocellulose; and
b) contacting a gel with the oil-in-water emulsion.

If the gel is a hydrogel or a hydrofiber, the oil-in-water emulsion may be added pre or post crosslinking of the hydrogel/hydrofiber.

Optionally, according to either the third or the fourth aspect, the nanocellulose is present in an amount within the range of from 0.1 to 3% by weight of the oil-in-water emulsion.

Optionally, with regard to either the third or the fourth aspect of the present disclosure, the one or more cellulose derivative(s) is/are present in the o/w emulsion in an amount within the range of from 0.5 to 5% by weight of the o/w emulsion.

Optionally, with regard to either the third or the fourth aspect of the present disclosure, the oil phase present in the o/w emulsion in an amount within the range of from 10 to 50% by weight of the o/w emulsion, such as from 15 to 30% by weight of the o/w emulsion.

Optionally, with regard to either the third or the fourth aspect of the present disclosure, the step of contacting said carrier material with said oil-in-water emulsion may be performed by spraying, impregnation, coating or mixing the the oil-in-water emulsion with the carrier material.

Optionally, with regard to either the third or the fourth aspect of the present disclosure, the step of providing an oil-in water emulsion comprising or consisting of oil droplets dispersed in an aqueous phase comprising one or more cellulose derivatives and nanocellulose (i.e. "step a" in the method according to the third aspect and fourth aspect, respectively), further comprises the steps of:
a) providing an aqueous phase by mixing water, one or more cellulose derivative(s) and nanocellulose;
b) optionally, adding an electrolyte to said aqueous phase, before or after adding said one or more cellulose derivative(s) and nanocellulose;
c) providing an oil phase by adding an oil to said aqueous phase;
d) homogenizing said aqueous phase with said oil phase;
e) optionally, adding a further cellulose derivative, being a different cellulose derivative from the one(s) comprised in the aqueous phase in step a), to the oil-in-water emulsion and subjecting the oil-in-water emulsion to an additional homogenization step.

Optionally, the electrolyte in step b) is a divalent cation, such as $Ca^{2+}$, $Mg^{2+}$, $Mn^{2+}$ and $Zn^{2+}$.

Optionally, the electrolyte is added in an amount providing a concentration of least 0.01 Molar in said aqueous phase. Optionally, the electrolyte is added in an amount of at least 0.05, such as from 0.01-0.5 Molar.

Optionally, the nanocellulose is nanocrystalline cellulose.

Optionally and if needed step e) of adding a different cellulose derivative from the one(s) comprised in the aqueous phase in step a) may be included to increase the stability of the oil-in-water emulsion.

A fifth aspect of the present disclosure relates to a method of producing a medical dressing comprising the steps of;
a) producing a combined carrier material and composite material according to the third aspect of the present disclosure; and
b) incorporating said combined carrier material and composite material into a medical dressing.

A sixth aspect of the present disclosure relates to a method of producing a medical dressing comprising the steps of;
a) producing a carrier material in the form of a gel, such as a hydrogel or a hydrofiber, comprising an oil-in-water emulsion according to the fourth aspect of the present disclosure, and;

b) incorporating said gel comprising an oil-in-water emulsion into a medical dressing.

BRIEF DESCRIPTION OF THE DRAWINGS

FIG. 1b illustrates an enlarged view of the composite material as disclosed herein, taken from FIG. 1a;

DETAILED DESCRIPTION

The present disclosure thus relates to a medical dressing comprising a carrier material and a composite material. The composite material comprises oil droplets dispersed in a matrix. The matrix comprises one or more cellulose derivatives and nanocellulose.

The carrier material according to the present invention may be a foam structure, such as for example, an open-cell foam or a closed-cell foam that comprises through-holes. Non-limiting examples of suitable polymer foams include polyurethane foams, polyvinyl alcohol foams, silicone foams, polyolefin foams, alginate foams, and combinations thereof. In some embodiments, the polymer foam comprises a polyurethane foam. Non-limiting examples of suitable polyurethane foams include polyester-based and polyether-based foams. As a non-limiting example, AVANCE™ Foam sold by Mölnlycke Health Care is made of a hydrophobic reticulated polyurethane foam with a large open cell structure.

The carrier material may also be a net structure, such as a low-adhering net made by e.g. a woven or a knitted fabric comprising for example polyamides, polyesters, polyolefins, cellulose-based polymers and polyurethans. Also a fibrous structure such as a nonwoven material, e.g. spunbond, meltblown, carded, hydroentangled, wetlaid nonwovens etc. may be used. Suitable nonwoven materials can be composed of natural fibres, such as wood pulp or cotton fibres, man-made fibres, such as polyester, polyethylene, polypropylene, viscose etc., or from a mixture of natural and syntethic fibres. A film such as a polymeric film, e.g. a polyurethane, polyolefin, polyester or polyamide film may also act as a carrier material according to the present disclosure.

Figure 1A:
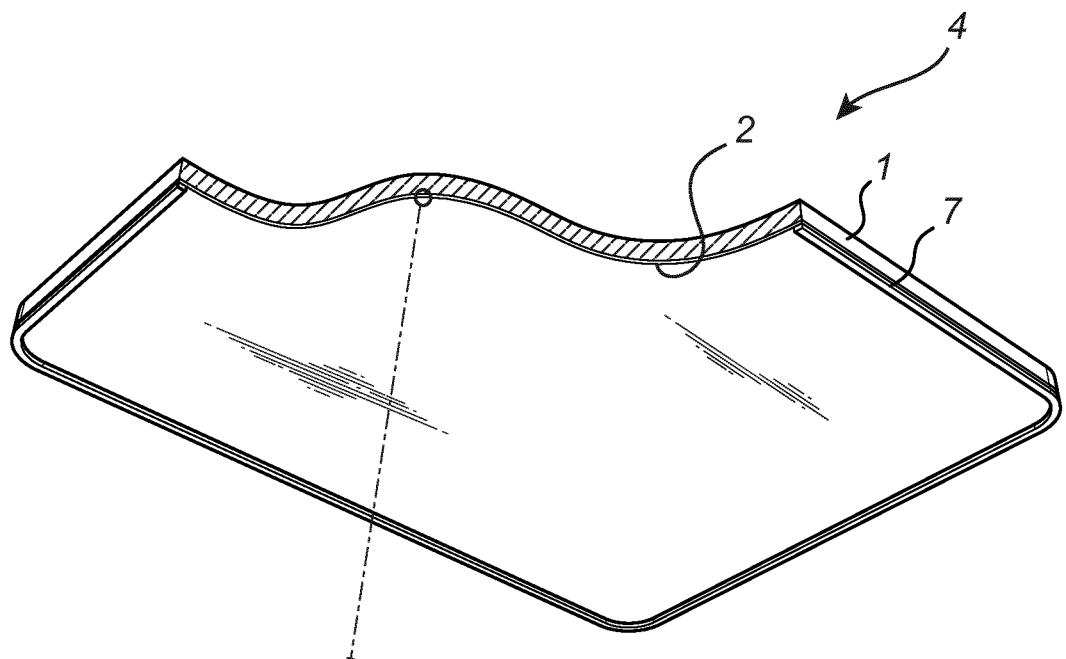
FIG. 1a illustrates a schematic perspective view a medical dressing according the the present disclosure.
Figure 1B:
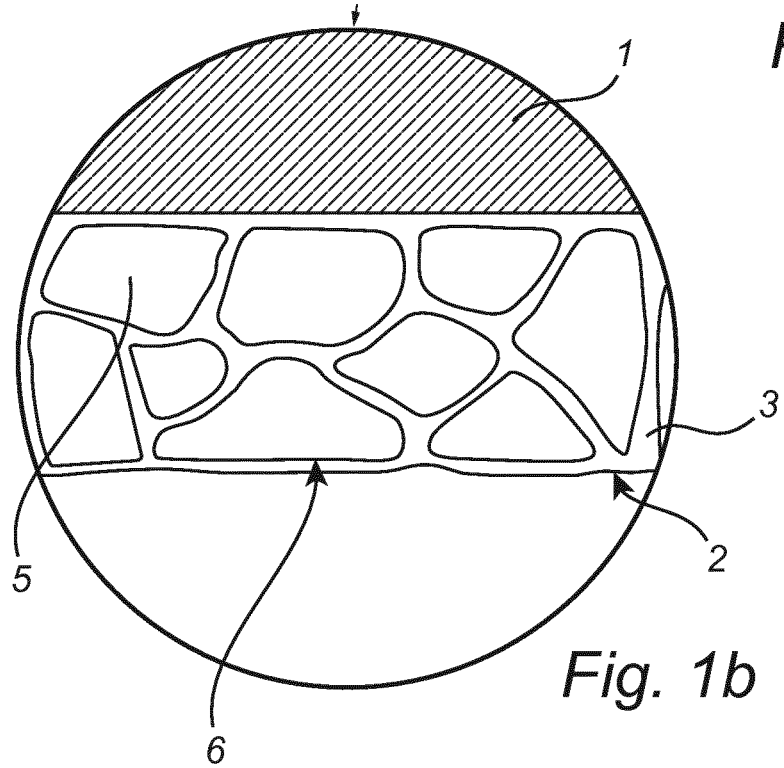

FIG. 1a illustrates an embodiment of a medical dressing 4 as disclosed herein, wherein the carrier is a vapour permeable film carrier 1 coated with a continuous layer of the composite material 2. In FIG. 1b, which is an enlarged view of the composite material 2 taken from FIG. 1a, the composite material 2 comprises oil droplets 5 dispersed in a matrix 3 thereby forming an interface 6 between each of the oil droplets 5 and the matrix 3. The matrix 3 comprises one or more cellulose derivative(s) and nanocellulose. In the embodiment as disclosed in FIG. 1b, the matrix 3 is enriched by nanocellulose at the interface 6 (i.e. at the surface of the oil droplets). The medical dressing 4 disclosed herein further comprises an adhesive border 7 to adhere the medical dressing 4 to a dermal surface.

The composite material or o/w emulsion may also be included in a gel, such as a hydrogel or a hydrofiber, acting as a carrier material, or other substantially dilute systems, and be used as a medical dressing. Suitable polymers which may form hydrogels are alginates, polyacrylic acid (PAA), poly(N-isopropyl acrylamide), chitosan, hyaluronic acid, polyvinyl alcohol (PVA), or proteins, such as collagen. The o/w emulsion may be added pre or post crosslinking of the hydrogel. The crosslinking of the hydrogel is either performed by adding a crosslinker for chemical crosslinking or for the creation of junction zones.

If the emulsion is added pre crosslinking of the hydrogel, 0.1-30 wt. % emulsion (wet) may be added to the solution. In the case of alginates, the divalent calcium ion in $CaCl_2$ will contribute to the creation of junction zones and create calcium alginate gels with droplets of emulsion between these junctions.

When adding the emulsion post crosslinking of the hydrogel, the hydrogel will absorb the emulsion. This procedure is comparable to impregnating the material, where the droplets of emulsion are distributed homogenously in the hydrogel. The amount of added emulsion may thus be 0.1-10 wt. % of the hydrogel. However, if a more rigid hydrogel, i.e. with a higher degree of cross-linking is needed, the emulsion may be used a softener and be added in amounts of from about 10-30 wt. % of the hydrogel.

The composite material may also be included in, such as dispersed in or coated on to, a silicone based or acrylic adhesive acting as the carrier and suitable for use in medical dressings, non-limiting examples on suitable adhesives are two-component RTV systems such as Q72218 (Dow Corning) and SilGel 612 (Wacker Chemie AG). The composite material may for example be added in powdered form on the silicone based or acrylic adhesive and/or dispersed within the silicone based or acrylic adhesive or may also be mixed with the adhesive as an emulsion. The emulsion may for example be added either to component A or B in the two-component adhesive before curing. The suitable amount of composite material in such a silicone based or acrylic adhesive is from 5-30 wt %.

Many known wound dressings include a self-adhering adhesive, also known as pressure-sensitive adhesive (PSA), which purpose is to adhere to the wound and/or to the skin surrounding the wound and thus to fixate the dressing in a desirable position. Various adhesives are being used for affixing medical products on the skin, some of the most common being encompassed by the terms acrylic adhesives and silicone based adhesives, among others. Such adhesives may also be suitable to use in or on a carrier as disclosed herein.

The composite material may be coated or deposited onto an acrylic or silicone based adhesive. A coating of the composite material, for example in powder form, on an adhesive material as disclosed herein needs to be high enough in concentration to give effect (on skin, wound or infection) but low enough to still retain the adhesive properties, if such is desired. Hence, a suitable thickness of the layer provided by coating/deposition may be within the range from 1 to 500 μm, optionally from 10 to 100 μm. The concentration of composite material per area of carrier material may be within the range from 0.05 to 3 $g/m^2$, optionally within the range from 0.15 to 0.80 g/m². The adhesive is in contact with the skin or the wound and should therefore be a silicone based or acrylic adhesive suitable for application in a medical dressing. Such adhesives forms often part of secondary carrier materials in medical dressings, such as a foam carrier, nonwoven carrier, a net carrier, superabsorbents, hydrogel, a film carrier, a wound dressing or prevention dressing, such as the dressings sold under the trademarks Mepilex® Border, Mepilex® Border Ag, Mepilex®, Mepilex® Ag, Mepitel®, Mepore® by Mölnlycke Healthcare AB.

When the carrier material for the composite material is a gel, such as a hydrogel or a hydrofiber, an organogel or a silicone gel, the gel may be further applied to an additional carrier material structure such as foam, net, nonwoven material or film to provide a medical dressing. The gel may be applied as a layer, such as by coating, on the foam, net, nonwoven material or film to provide for a medical dressing.

The medical dressing as disclosed herein may be prepared by incorporating the composite material into the carrier material or applied to a surface thereof. The carrier material may be coated either by redissolving the composite material, such as by adding water, or prior to drying the o/w emulsion. The o/w emulsion may for example be coated onto a carrier material by means of spray coating, extrusion, dipping, impregnation and/or spreading. The composite material may also be incorporated into the carrier material, such as for example when the carrier material is an adhesive, a gel, such as a hydrogel, a hydrofiber, or during preparation of the foam or such as during extrusion of a film, fibers or net.

The carrier material coated/treated with the o/w emulsion is subsequently dried, such as by means of heating. In a production line the carrier material may be carried by means of a conveyer belt in a manufacturing process, and heat may be applied to the conveyer belt. The coated carrier material may also be dried in a separate drying step post-coating, such as in an oven.

The oil-in-water emulsion may also be spray dried to provide a dry composite material powder, which may be powder coated onto the carrier material.

Preparation of the Composite Material

Materials Used in the Preparations of the Composite Material

Materials used were; Microcrystalline cellulose (MCC), Avicel PH101. Carboxymethyl cellulose sodium salt (Sigma Aldrich) Mw=90000; d=1.59. HPMC 60SH-50 50cP type 2910 (Shiu ETSU Chemical). HPMC 90SH-100 100cP type 2208 (Shiu ETSU Chemical). HPC-SSL Mw=40000 (Nisso Chemical) HEC 250 G PHARM Natrosol sample. HEC 250 HHX PHARM Natrosol. EHEC Bermocoll E230 FQ (Akzo Nobel). MC Methocel A4M Premium (Dow Chemicals). Dodecane Reagentplus >99% (Sigma Aldrich). Hexadecane Reagentplus >99% (Sigma Aldrich). Ion exchange resin, Dowex Marathon C-Hydrogen (Sigma Aldrich). Fluorescein isothiocyanate isomer I (Sigma Aldrich).

Isolation of Crystalline Nanocellulose

The CNCs used were isolated from microcrystalline cellulose by first adding 40 g of MCC to a 2 liter Erlenmeyer flask containing 400 ml milli-Q water (resistivity 18.2 MΩ) under constant stirring. 389 ml of sulphuric acid (95-97%) was then added drop wise to the flask over a period of 30 minutes whilst the flask simultaneously was being surrounded by an ice slurry to ensure that hydrolysis did not occur until all the acid has been added. The flask containing the acid and the MCC-suspension was then heated to 45° C. The reaction was continued at 45° C. for two hours after which the slurry was poured into a 5 liter Erlenmeyer flask containing 4 liters of deionized water upon which the reaction was quenched.

The slurry containing CNCs, amorphous remnants from the MCC and sulphuric acid was portionally centrifuged (Heraens Megaforce 40, Thermo scientific) at 3900 rpm for 15 minutes upon which the supernatant was discarded and replaced with additional slurry whilst shaking vigorously to disperse solid content at the bottom of the vessel. This process was later repeated twice by replacing supernatant with deionized water to ensure that amorphous, water-soluble by-products had been separated from the CNCs. The centrifuged CNCs were transferred into a dialysis membrane (Spectrapor Dialysis membrane tubing, MWCO: 12:14.000) and placed in a tank containing deionized water where it was left for approximately two weeks. The water in the tank was changed twice a day to ensure elimination of as many free ions as possible.

The CNCs were after dialysis dispersed in deionized water and sonicated (Ultrasonic Processor model VC505, Sonics Vibra-cell) for 14 minutes at an amplitude of 4% to ensure that the individual nanocrystals were separated from a potential aggregated state. The vessels containing the suspension during sonication were furthermore surrounded by ice to prevent overheating from the excess input of energy. 10-15 lab spoons of ethanol cleaned ion exchange beads (Dowex Marathon C-hydrogen) were added to the newly sonicated suspension of CNC to eliminate the remaining free ions. The suspension was left for two days under stirring after which the suspension was titrated with 0.1M sodium hydroxide to minimize the conductivity. The dilute suspension of CNCs was rotary evaporated (Büch rotavapor R-200) to a final concentration of no more than 4% to ensure colloidal stability and manageable viscosity of the CNC-suspension.

CNCs with a length and width of at least 234±66 nm and 30±7 nm respectively were isolated from MCC. The dimensions are dependent on the degree of hydrolysis reached during isolation which can be varied by choice of acid, concentration of acid and stirring mechanism during hydrolysis. The dimensions are furthermore not only differing from batch to batch, various degrees of polydispersity as a result of inhomogeneous distribution of acid throughout the bulk of the microfibrils can also be identified.

As understood by the skilled person in the art, the crystalline nanocellulose may of course be isolated according to other known methods.

Cellulose Derivatives

Cellulose derivatives were chosen based on their performances as additives in emulsion formulations with CNCs. A summary of studied CDs can be seen in table 1 below. Performances were based on visual observation where an unstable or unsuitable emulsion simply was referred to as "–". Some emulsions were seemingly stable in the wet state but not during drying and was therefore also referred to as "–" or "+" in the dry emulsion column. A stable o/w emulsion is an emulsion which may hold the oil dispersed. If the emulsion is unstable, an oil layer will accumulate on the surface which will be seen visually. If the oil droplets ends up very large, such as for example 500 µm, if the droplets coalescence or if the oil-in-water emulsion does not dry to a composite material these are also signs of unstable and unsuitable emulsions.

TABLE 1

Available CDs which were tested as components in emulsions and solid emulsions.

| CD | Viscosity (mPas (2%)) | Emulsion | Dry emulsion/ composite material |
|---|---|---|---|
| Methyl Cellulose | 4000 [30] | + | − |
| Hydroxypropyl Methyl Cellulose | 50 [33] | + | + |
| Hydroxypropyl Methyl Cellulose | 100 [33] | + | + |
| Hydroxyethyl Cellulose HHX | 4500* [31] | − | − |
| Hydroxyethyl Cellulose G | 250-400 [31] | + | + |
| Carboxymethyl Cellulose | 50-200** [32] | + | + |
| Ethyl Hydroxyethyl Cellulose | >400 | + | + |
| Hydroxypropyl Cellulose Grade SSL | <50 [34] | + | − |

"+" indicates success and "−" indicates failure. Viscosity of CDs also apparent.
*viscosity measured for a 1% solution.
**viscosity measured for a 4% solution.

Preparation of the Oil-In-Water Emulsion

The cellulose derivative(s) as disclosed herein and above were diluted in Milli-Q (18.2 MΩ) to manageable viscosities that wouldn't hinder emulsification, usually corresponding to a solution of 4-7 wt. %, depending on the type of CD chosen. The actual concentration of the CDs was measured gravimetrically.

Emulsions were prepared by adding CD solution to a plastic vial (50 ml) containing the CNC-suspension. Calcium chloride 0.1M solution was then added together with additional Milli-Q to meet the requirements on the appropriate oil/water ratio.

The oil phase was added on top of the water phase, after which emulsification and homogenization was performed using diax 900 homogenizer (Heidolph Instruments) at a speed of 22000-23000 rpm. The mixture of oil and water phase was homogenized for 5 minutes.

Composite Material/Dry Emulsion Preparation

Composite material according to the present disclosure were derived from polymer pickering emulsions prepared according to the above under "Preparation of the o/w emulsion", by pouring the emulsions into petri dishes and allowing them to dry. The amount of time required for an emulsion to dry was tracked gravimetrically where a steady state occurred, according to FIG. 2, when all of the water had been assumed to have left the emulsion since the mass ratio did not change as a function of time.

Figure 2:
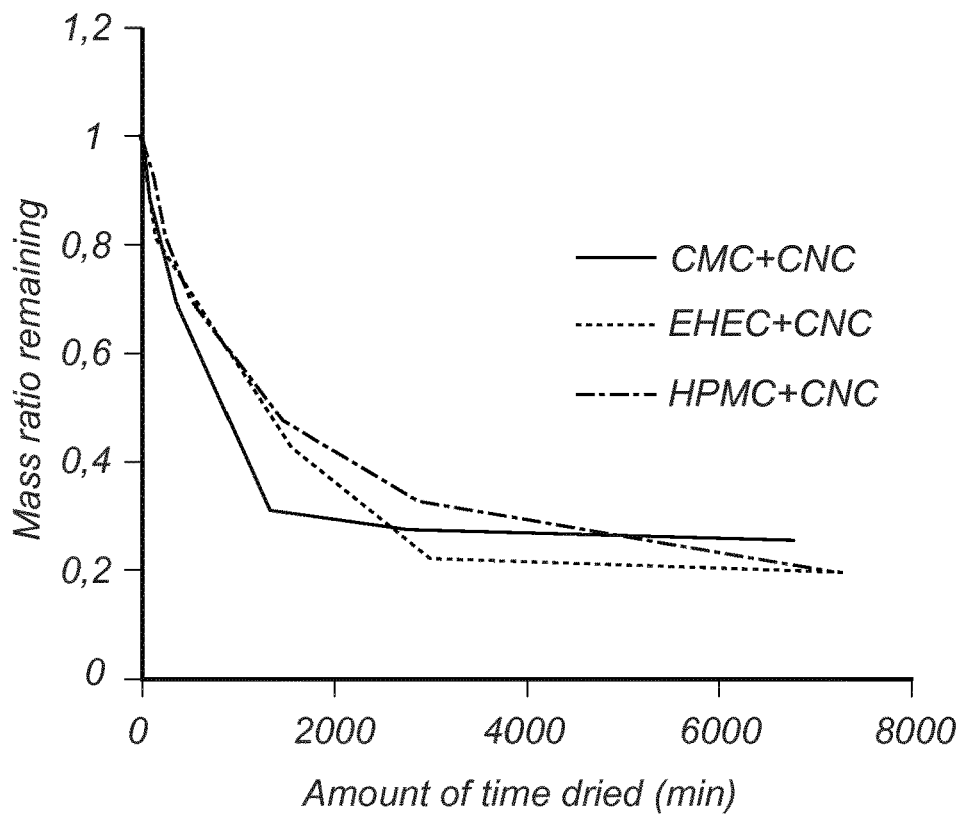
FIG. 2 illustrates the rate of solvent casting from emulsions made with three different cellulose derivatives.

The rate of solvent casting from emulsions made with three different cellulose derivatives in petri dishes is shown in FIG. 2. Dry emulsions assumed to be ready for characterization when the mass ratio in the petri dish did not change as a function of time. The mass of the individual emulsions were between 20 and 23 grams.

Redispersion of the Composite Material

Figure 3:
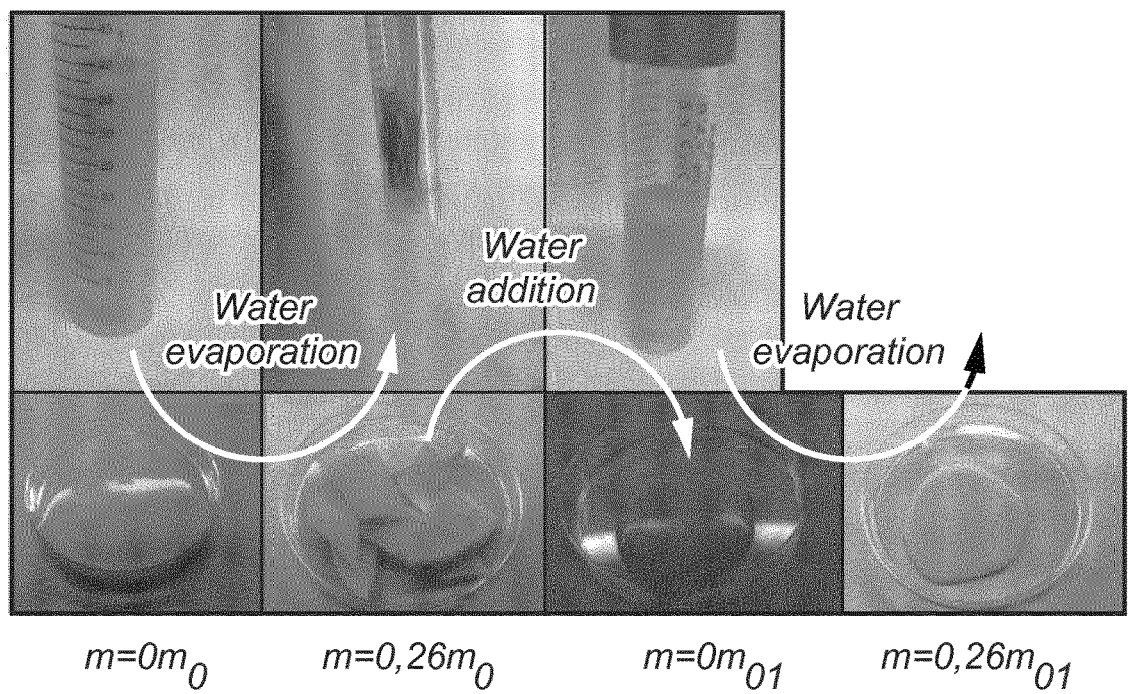
FIG. 3 illustrates the redispersion of the composite material.

The amount of water evaporated from emulsions during transformation to solid emulsions may be tracked gravimetrically if redispersion is to be done. Redispersion of a stable composite material may be done by adding the same amount of water that have evaporated to a plastic vial containing the composite (broken up in pieces). The vial may be left for a day to make sure redispersion of the solid emulsion to an emulsion is fully complete and not influenced by energy input which would create new interfaces rather than maintaining the original ones. The emulsion was after complete redispersion (determined visually) poured into a petri dish and left to dry. See FIG. 3, wherein the first step, the water evaporates, in a second step water is added and the composite material is redispersed and in a final and third step it may be seen that by evaporating the water the composite material may again be produced.

As may be seen, the composite material as disclosed herein is a highly flexible composite material which may be produced and dried and in a later and separate step, be applied to a carrier material to produce a medical dressing as disclosed herein.

Characterization of the Materials

Atomic Force Microscope (AFM)—Characterization of CNC

Pieces of mica were cut and freshly cleaved using double-sided tape. A few drops of 0.1 wt. % cationic polyethylenimine (PEI, Mw=40000 g/mole) were added to the mica plate prior to the addition of CNC to ensure adhesion of the negatively charged specimens to the plate. The mica plate containing PEI was dried with nitrogen after which a few drops of a 0.05 wt. % CNC-suspension was added and dried with nitrogen in a similar manner. The PEI and CNC-suspension were let to rest only one minute before drying with nitrogen to ensure no aggregation would occur, that if present would make sizing difficult. AFM was performed (NT-MDT Atomic Force Microscope) using silicone cantilevers with a golden reflective side and a force constant of 1.45-15.1 N/m in a semi-contact mode. Micrographs were analyzed to determine the dimensions of the isolated nanocrystals.

Light Microscopy—Characterization of Emulsions

Light microscopy was performed by adding a few drops of fresh emulsion into a plastic vial, after which the emulsion was diluted with appropriate amount of distilled water. The amount of water used was determined visually based on the turbidity so that the emulsion droplets would be distinguishable whilst still showing a statistically relevant amount of droplets.

The size of the emulsion droplets was determined by optical microscopy.

Multiple Light Scattering (MLS)

Emulsions were analyzed within 10 minutes of production by pouring fresh polymer pickering emulsions in customized tubes that were then inserted in a Turbiscan MA2000. The magnitude of backscattered light, both initial and time dependant, was collected over a specific length interval in the tube. The length interval was chosen to make sure variations in light intensity were meaned over a suitable set of data points. Initial magnitude of backscattered light was collected to get information regarding the average relative droplet size in the emulsions, whereas time dependent (over 24 hours) were means to assess the relative stability of the emulsions.

Composite Material/Dry Emulsion Compression Tests

Initial experiments were made and suggest that the following examples would be suitable for application in a medical dressing as disclosed herein.

Composite material Ex.1: 2% CMC 0.5% CNC 20% Paraffin oil

Composite material Ex.2: 2% HPMC 0.5% CNC 20% Paraffin oil

Composite material Ex.3: 2% HPMC 0.5% CNC 20% Silicone oil

Composite material Ex.4: 1.52% HEC 0.48% HPMC 0.5% CNC 20% Silicone oil

These four emulsions were dried to composite materials and punched into 15 mm diameter discs, with a thickness ranging between 0.7-1.5 mm, and compressed at a rate of 0.5%/s to various strains between 20-99%. Results that were obtained from the testing was i) Stress-strain relationship for the four solid emulsions and ii) mass loss (i.e. oil release) as a function of strain rate. The results are described in respective figure below.

Figure 4:
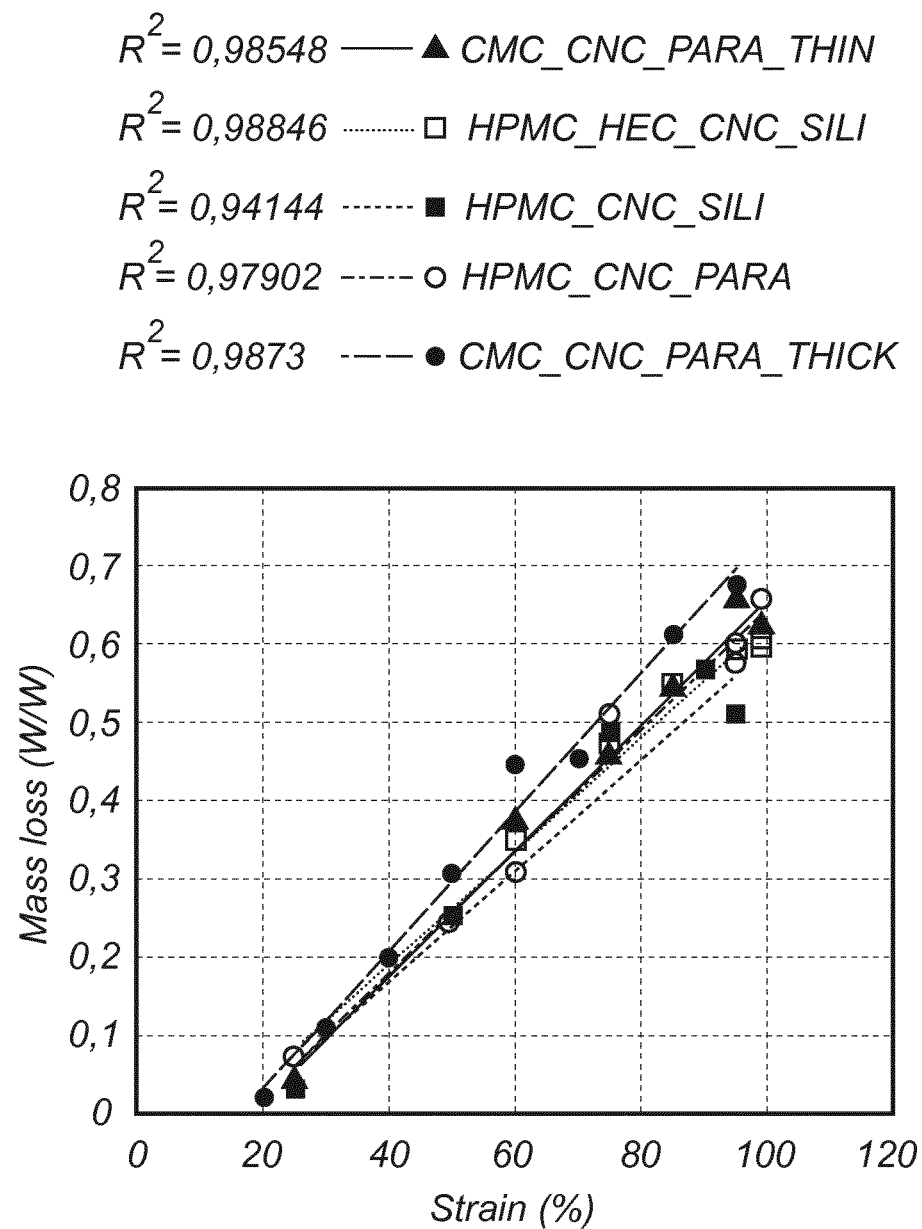
FIG. 4 illustrates mass loss due to oil leakage upon compression of the composite material.

FIG. 4 is an illustration of mass loss due to oil leakage upon compression of the composite materials. The oil release was rather linear after 20% strain as shown by $R^2$-values. The relatively low amount of oil release at, and prior to 20% strain can be explained by the stiffness of the material, which still is prominent at low strain percentages for each of the composite materials. There is a shift in stress-strain behavior around 20% strain for each sample, which corresponds to when a linear oil release behavior starts to become apparent. The discs lost around 70% mass when compressed fully, which indicates very good encapsulation of the oil, considering some oil was lost on the surface of the samples and during sample preparation (punching of the discs).

Figure 5:
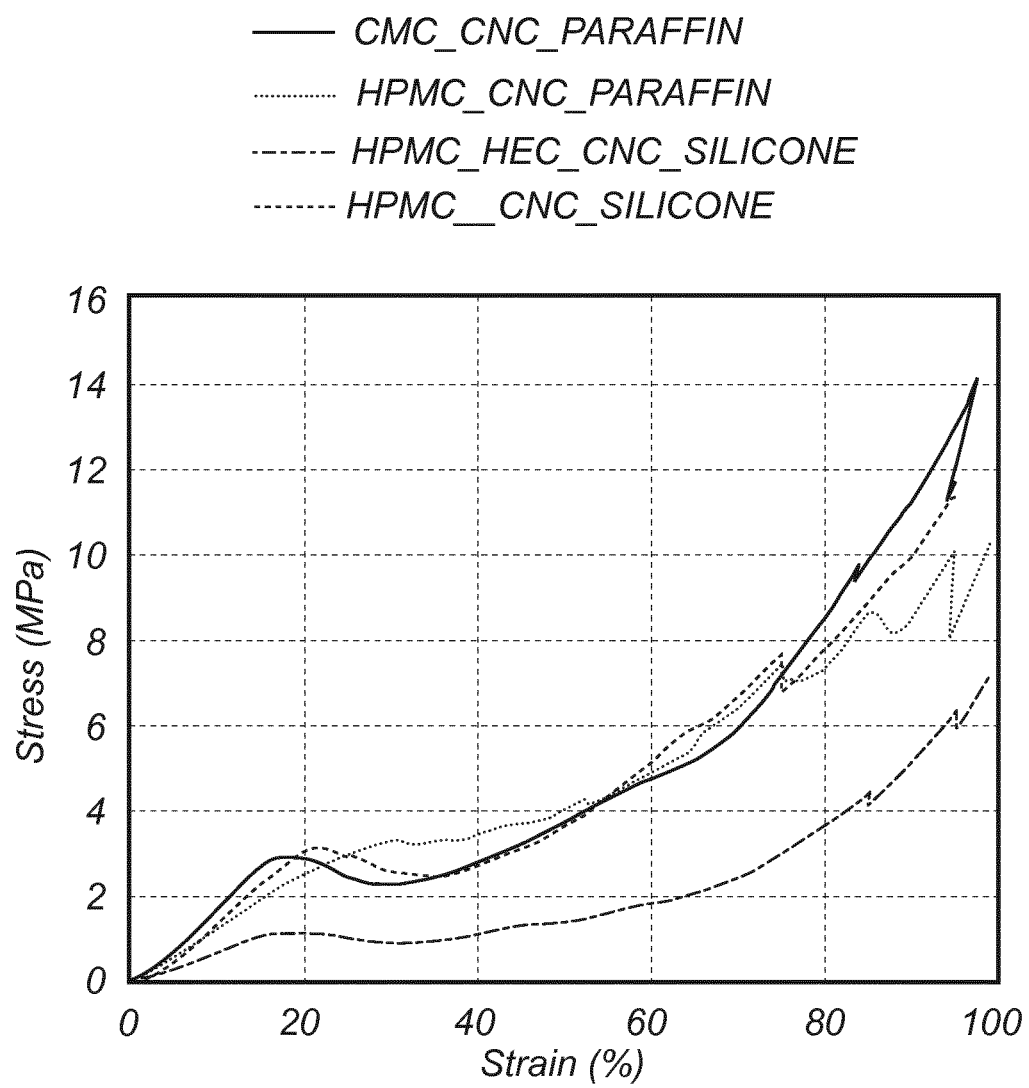
FIG. 5 illustrates a graph of the compressive stress vs strain relation of composite materials.

FIG. 5 illustrates a stress vs strain curve for the composite materials Ex. 1-4. It is noted that the HPMC-HEC-CNC emulsion is significantly softer than the rest, even despite containing equal amounts of oil with similar release trend. The curves were obtained from a mean value of eight different compression tests for each specimen.

For venous leg ulcers and other chronic wounds it is conventional to apply rather low pressures, such as around 40 mm Hg on the medical dressing, which is less than 0.01 MPa. For patients with a risk of pressure ulcers, the force may be somewhat higher than 0.01 MPa. This means that the pressure exerted to the composite material in the medical dressin is relatively low. However, the strain at low level still induces a release of oil of approximately 5-10 wt % as a burst release.

This mechanism is of importance for regulation of the controlled and sustained release for both wound and tissue (such as antimicrobial substances/oils for wounds or nurturing oils/vitamins for pressure ulcer prevention). Sustained release is necessary for the tissue site not to contain an exaggerated amount of oil, since this may affect the adhesion of the adhesive for maintaining the medical dressing correctly positioned.

Additionally, the release of substances, such as antimicrobial substances or antimicrobial oils needs to be controlled after the initial burst release of actives, in order to maintain a low toxicity for mammalian cells. Consequently, the dressing material will, after a pressure has been applied, act as a reservoir, which either will dissolve in a sustained manner when in contact with sweat (slowly) and/or wound exudate (faster).

As the patient moves the pressure will change over the dressing material, allowing for release in a new area of the dressing and a continuous release of active substance(s) for as long as it is needed.

EXAMPLES

The following examples illustrate medical dressing prepared according to the present disclosure without limiting the same.

Example 1

Oil-in-water emulsions were prepared in accordance with the method described above, i.e. cellulose derivative(s) (CD) was dissolved in a 0.1 M $CaCl_2$ aqueous solution in an amount providing a concentration within the range of from 1 to 3 wt. % of the resulting emulsion. Nanocrystalline cellulose (CNC) was dissolved in the same solution in an amount providing a concentration within the range of from 0.3 to 1.0 wt. %, based on the total weight of the o/w emulsion. Alternatively, the CNC may be dissolved in 0.1 M $CaCl_2$ solution before mixing the CNC solution with the solution comprising the CD solution. An oil phase was then provided by adding the oil to the aqueous solution, all oil at once or to pipette the oil into the solution while the homogenizer is on and stirring of the solution in the homogenizer to create the emulsion, 22 000-24 000 rpm for 5 minutes with an ULTRA-TURRAX® T25.

In these examples the cellulose derivative used was HPMC, Metolose from Shiu Etsu, 50 cps, and CNC, produced according to the method above, was used to provide the encapsulation of the oil droplets.

Four different oils were used in the examples;
Oil 1: Ondina oil (paraffin oil), Ondina X430 from Shell
Oil 2: Corn oil, Sigma Aldrish
Oil 3: Canola oil, Sigma Aldrish
Oil 4: Silicone oil, Belsil DM350 deom Wacker Chemie

TABLE 5

| Ex. | Oil | Weight % HPMC | Weight % CNC | Weight % oil | Weight % water (before drying) |
|---|---|---|---|---|---|
| 1 | Oil 1 | 2.00% | 1.00% | 20.00% | 77.00% |
| 2 | Oil 1 | 2.06% | 0.34% | 20.60% | 77.00% |
| 3 | Oil 1 | 1.07% | 0.53% | 21.40% | 77.00% |
| 4 | Oil 1 | 1.09% | 0.18% | 21.73% | 77.00% |
| 5 | Oil 2 | 2.00% | 1.00% | 20.00% | 77.00% |
| 6 | Oil 2 | 2.06% | 0.34% | 20.60% | 77.00% |
| 7 | Oil 2 | 1.07% | 0.53% | 21.40% | 77.00% |
| 8 | Oil 2 | 1.09% | 0.18% | 21.73% | 77.00% |
| 9 | Oil 3 | 2.00% | 1.00% | 20.00% | 77.00% |
| 10 | Oil 3 | 2.06% | 0.34% | 20.60% | 77.00% |
| 11 | Oil 3 | 1.07% | 0.53% | 21.40% | 77.00% |
| 12 | Oil 3 | 1.09% | 0.18% | 21.73% | 77.00% |
| 13 | Oil 4 | 2.00% | 1.00% | 20.00% | 77.00% |
| 14 | Oil 4 | 2.06% | 0.34% | 20.60% | 77.00% |
| 15 | Oil 4 | 1.07% | 0.53% | 21.40% | 77.00% |
| 16 | Oil 4 | 1.09% | 0.18% | 21.73% | 77.00% |
| 17 | Oil 1 | 1.42% | 0.35% | 21.23% | 77.00% |
| 18 | Oil 1 | 1.42% | 0.35% | 21.23% | 77.00% |
| 19 | Oil 1 | 1.42% | 0.35% | 21.23% | 77.00% |

The examples 1-6, 9-10, 13-14 and 17-19 were successfully provided as composite materials with desired mechanical properties, such as a relatively high to high mechanical strength and resistance to mechanical deformation.

Silicone Based Adhesive Coated Onto a Polyurethane Film

In this example a polyurethane film was coated with a silicone based adhesive comprising 5 wt. % composite material. The silicone based adhesive was a typical two-component silicone addition-curing polysiloxane system, comprising vinyl-functional polysiloxanes in both components (A and B), a platinum catalyst in one of the components (A) and hydride-containing polysiloxanes in the other component (B).

Figure 6:
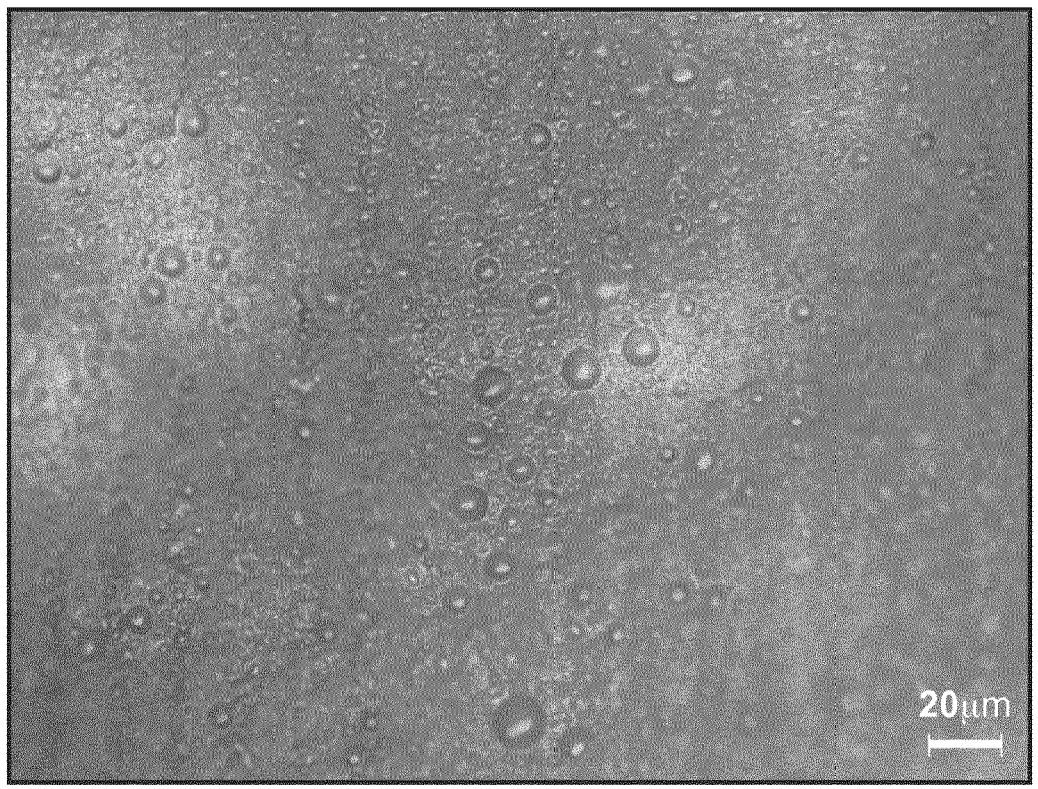
FIG. 6 illustrates a silicone based adhesive coated with the composite material.

18 g of component (A) of the polysiloxane system described above was mixed with 2 g of composite material, Ondina Oil, 0.5 wt % CNC and 2 wt % HPMC, and the mixture was homogenized for 30 s at 13 500 rpm using an Ultra-Turrax T25. 10 g of the resulting mixture was mixed with 9 g of component (B) using a speedmixer for 2 min at 2 000 rpm. The final mixture was coated onto a 20 μm polyurethane film and cured on a hot plate at 120° C. for 2 min. The result is illustrated in FIG. 6.

Polyurethane Foam Coated with Composite Material

Figure 7:
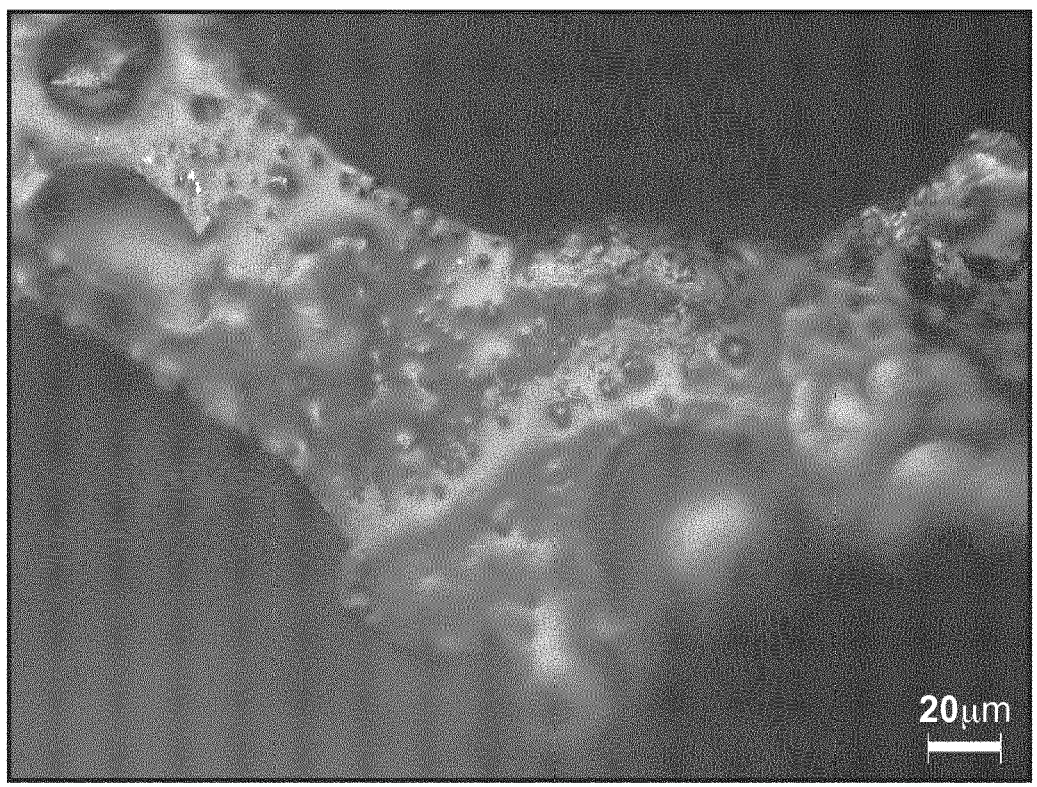
FIG. 7 illustrates a micrograph of a polyurethane foam coated with the composite material.

A 5 mm thick polyurethane foam provided on a conveyor belt was spray coated with an emulsion according to example 1 and 9 in an in-line process using an ultrasonic nozzle, while heating the conveyor belt to enable drying of the foam structure. The resulting coated polyurethane foam is illustrated in FIG. 7.

The water in the emulsion may also be evaporated until it is a thicker slurry, before spray coating it on the polyurethane foam. The emulsion may additionally be added to the polyurethane foam by means of a roll-to-roll process, immersion/dipping, or slot dye process, a further option is to spraydry the material, hence creating a dry powder of the emulsion, which can be powder coated onto the polyurethane foam.

Nonwoven Material Coated with Composite Material

A spunlace nonwoven material (30% viscose and 70% polyester) provided on a conveyor belt was spray coated with an emulsion according to example 1 and 9 in an in-line process using an ultrasonic nozzle, while heating the conveyor belt to enable drying of the nonwoven material.

The water in the emulsion may also be evaporated until it is a thicker slurry before spray coating it on the nonwoven material. The emulsion may additionally be added to the nonwoven material by means of a roll-to-roll process, immersion/dipping, or a slot dye process. A further option is to spraydry the material, hence creating a dry powder of the emulsion, which can be powder coated onto the nonwoven material.

A coating on a non-adhesive material, such as a polyurethane foam, nonwoven, hydrofibre, etc., can be thicker than on an adhesive. This type of coating will be more similar to an impregnation of the material. The limiting factor is the conformability of the material after the impregnation, since medical dressings need to be soft against the skin. If the material stiffens, it needs to be softened in the post process impregnation, or include a softening agent during impregnation. Impregnation may be performed on the side of the material closest to the tissue or wound, or on both sides. The concentration of the composite material may be between from 0.1 to 50 grams/m$^2$ on one side, or from 0.1 to 100 grams/m$^2$ if both sides are impregnated. The material may also be entirely soaked in the emulsion, with a concentration between 1-250 grams/m$^2$.

Hydrogel or High Water Content Material

The hydrogel was prepared by dissolving 3% alginate (Sigma Aldrich) in MilliQ water in a beaker while stirring at 90° C., the alginate being of medium chain length. The solution was cooled down before adding equal amounts of the pickering oil-in-water emulsion in a 0.1M $CaCl_2$/$CaCO_3$ buffer (ratio 1:1) using a blender or homogenizer followed by a short sonication. GDL (glucono-delta-lactone) was added using a blender for release of calcium ions from $CaO_3$ to promote crosslinking. The resulting hydrogel is an alginate hydrogel comprising 1.5% alginate.

According to this example, the oil-in-water emulsion is soaked or mixed into the hydrogel. However, the emulsion may also be applied by dipping or with an in-line spreading/smearing of the emulsion onto the hydrogel. The material may withstand a small increase in temperature for water removal, if needed.

The composite material may also be added as a dry powder and coated on top of the hydrogel.

Example 2

An assessment of the emulsion stability and mechanical testing of the composite material as disclosed herein was also made to confirm the emulsion stability and to verify that desired mechanical properties, such as a relatively high to high mechanical strength and resistance to mechanical deformation, were obtained for the composite materials.

All emulsions presented in this section contains 2.5% solid content, either 2.0% CDs+0.5% CNCs or 2.5% CDs. This specific concentration was based on the choice of CDs where it was found that appropriate CDs were not too viscous during emulsification whilst still estimated to be able to provide the composite material with sufficient amount of solid content.

Assessment of Emulsion Stability Using MLS

Figure 8:
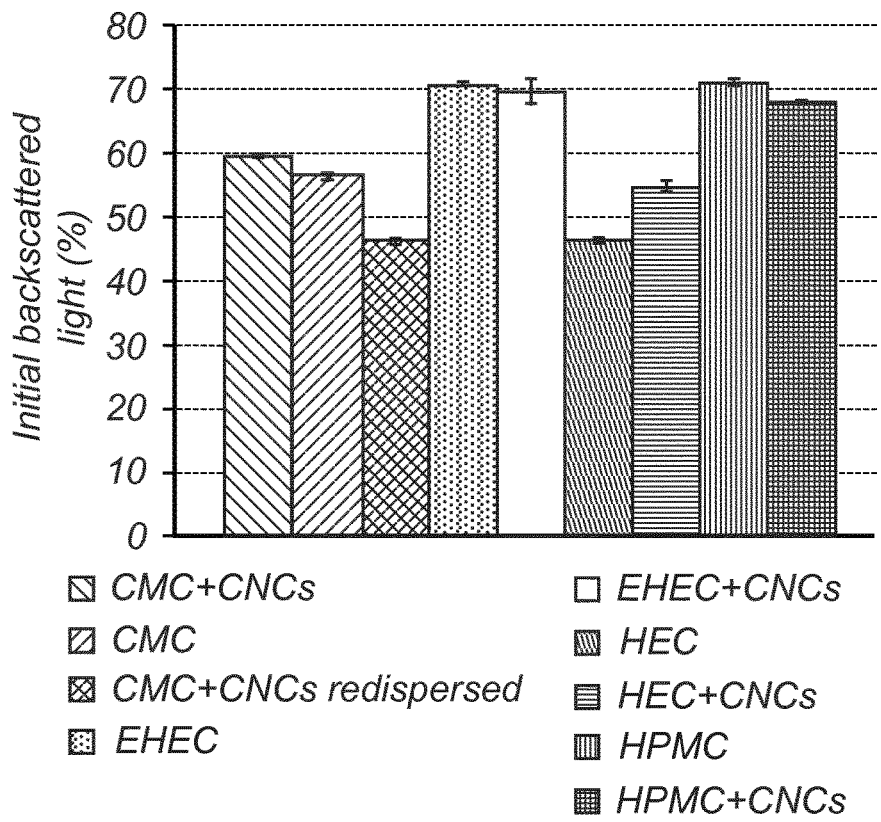
FIG. 8 illustrates the magnitude of the initial backscattered light of given emulsions.

FIG. 8 shows the magnitude of the initial backscattered light of emulsions with given composition of CDs and CNCs with a dodecane content of 25% wt. Also shown is the backscattered light of a redispersed CMC/CNC emulsion. Data was collected less than 10 minutes after emulsification.

The results from MLS in FIG. 8 reveal significant differences in initial oil droplet size amongst the emulsions with varying type of CDs. Emulsions produced with EHEC and HPMC exhibited smaller droplet sizes compared to those with HEC and CMC whereas EHEC and HPMC relative to each other were quite similar (68-70% BS). These emulsions only showed minor oil droplet size change (decline) with the addition of CNCs; indicating that the polymers played a major role in characteristic oil droplet size. For emulsions with HEC and CMC the trend was the opposite, though minor in the case of CMC; indicating that the CNCs were to a greater extent involved in the oil droplet character.

In order to characterize the relative stability of emulsions with varying CDs with and without CNCs, MLS was performed over 24 hours. Stability in this section refers to small amount of coalescence as indicated by small decrease in intensity of backscattered light over time. The relative stability of emulsions solely made with CDs ranked in the following order, as may be seen in see table 2 below, from the most stable to the least; CMC(1.1%)>EHEC(2.8%)>HPMC(4.1%)>HEC(46.3%). Emulsions with HEC showed phase separation after 24 hours; an observation which was not found in any of the other emulsions. The phase separation of emulsions solely stabilized with HEC in relation to the stability of the ones with HEC+CNCs shows interesting contrasts, which points on the role of the CNCs; to be active at the oil/water interface.

With the addition of CNCs (keeping the solid content constant) the stability ranking changed to CMC(0.6%)>HEC(1.9%)>EHEC(2.9%)>HPMC(5.6%). The stability of CMC and HEC emulsions were found to be enhanced by the addition of CNCs, though the relative enhancement of CMC emulsions was insignificant in comparison to HEC emulsions. HEC went from being completely unstable (46% decrease in BS) to one of the most stable (2% decrease in BS) with the addition of CNCs. The stability of EHEC was unaffected by the addition of CNCs with its minor change of 0.1% BS, whereas the one with HPMC decreased as indicated by the increase in difference from 4.1% to 5.6%.

Figure 9:
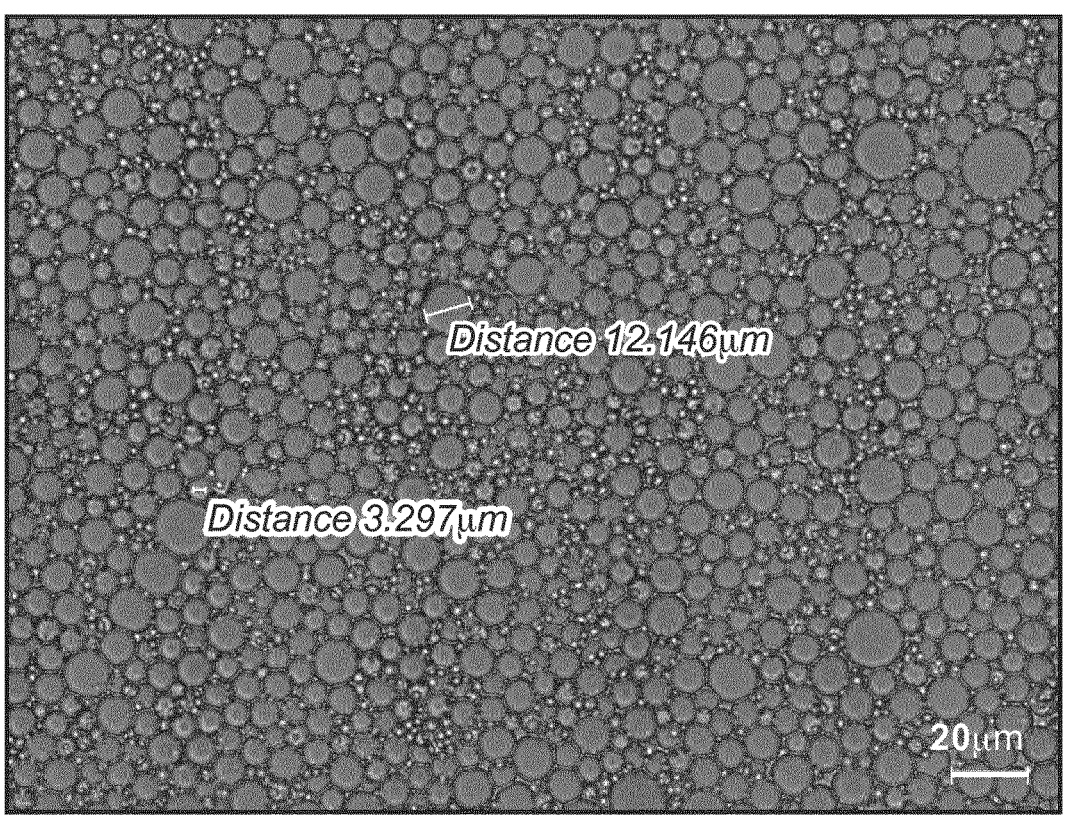
FIG. 9 illustrates a micrograph of a stable Pickering emulsion prior to drying.

The most stable emulsions were produced with CMC, and although CMC on its own produced extremely stable emulsions (2nd in stability rankings) it was shown that CNCs could enhance the stability even further (from 1.1% BS to 0.6% BS). FIG. 9 is a micrograph of a stable emulsion according to the present disclosure comprising Ondina oil, CMC and CNC.

TABLE 2

Difference in BS light over a time period of 24 hours for emulsions with given composition of CDs and CNCs. All emulsions were made with 25% dodecane. A large value in difference in BS over measured time period corresponds to a relatively unstable emulsion.

| Emulsion Composition | ΔBS |
|---|---|
| 2.5% CMC | 1.07 ± 0.25 |
| 2% CMC 0.5% CNC | 2.82 ± 0.23 |
| 2.5% EHEC | 0.57 ± 0.14 |
| 2% EHEC 0.5% CNC | 2.92 ± 0.46 |
| 2.5% HEC | 46.3 ± 0.25 |
| 2% HEC 0.5% CNC | 1.87 ± 0.74 |
| 2.5% HPMC | 4.08 ± 0.19 |
| 2% HPMC 0.5% CNC | 5.57 ± 0.30 |

It should be noted that all emulsions were enhanced by the presence of CNC, either through decreased coalescence or an increase in viscosity of original emulsions. The nature of Pickering emulsions coupled with the high aspect ratio of CNCs is believed to be the biggest factor for stability in both emulsions and solid emulsions.

The invention claimed is:

1. A medical dressing having a first side adapted to face a wound or tissue site when in use and a second side, opposite to said first side, said medical dressing comprises a carrier material and a composite material, wherein said composite material comprises oil droplets dispersed in a matrix, said matrix comprises one or more cellulose derivative(s) and nanocellulose.

2. The medical dressing according to claim 1, wherein said carrier material comprises a net, a foam, a fibrous structure, a film, a gel, a silicone based adhesive or an acrylic adhesive, or any combinations thereof.

3. The medical dressing according to claim 1, wherein said composite material is incorporated into said carrier material and said carrier material is provided on said first side of said medical dressing thus forming a wound or tissue contacting layer.

4. The medical dressing according to claim 3, wherein said carrier material has a first side, adapted to face a wound or tissue site when in use and a second side, opposite to said first side, and wherein said composite material is provided in a higher amount, based on weight, proximate to said first side of said carrier material than proximate to said second side of said carrier material.

5. The medical dressing according to claim 3, wherein said medical dressing further comprises a support layer and wherein said wound or tissue contacting layer has a no load thickness of from 0.1 mm to 10 mm.

6. The medical dressing according to claim 5, wherein said carrier material is silicone based adhesive.

7. The medical dressing according to claim 1, wherein said composite material forms a, continuous or discontinuous, layer on said carrier material and wherein said composite material is provided on said first side of said medical dressing thus forming a wound or tissue contacting layer.

8. The medical dressing according to claim 1, wherein said medical dressing comprises a cover layer, provided at a second side of said medical dressing.

9. The medical dressing according to claim 1, wherein said medical dressing comprises said composite material in an amount ranging from 0.01 to 600 g/m² of said carrier material.

10. The medical dressing according to claim 1, wherein said nanocellulose is nanocrystalline cellulose.

11. The medical dressing according to claim 1, wherein said one or more cellulose derivative(s) is/are cellulose ether derivative(s).

12. A medical dressing having a first side, adapted to face a wound or tissue site during use, and a second side, opposite to said first side, said medical dressing comprises a carrier material in the form of a gel, said gel comprises an oil-in-water emulsion comprising oil droplets dispersed in an aqueous phase comprising a matrix, said matrix comprises one or more cellulose derivatives and nanocellulose.

13. The medical dressing according to claim 12, wherein said carrier material has a first side, adapted to face a wound or tissue site when in use and a second side, opposite to said first side, and wherein said oil-in-water emulsion is provided in a higher concentration, based on weight, proximate to said first side than proximate to said second side of said carrier material.

14. A method of producing a combined carrier material and composite material for use as a component in the medical dressing according to claim 1, comprising the steps of;
 a) providing an oil-in water emulsion comprising or consisting of oil droplets dispersed in an aqueous phase comprising one or more cellulose derivatives and nanocellulose;
 b) contacting a carrier material with said oil-in-water emulsion; and
 c) drying said oil-in-water emulsion until 50-100% by weight of the water comprised in said oil-in-water emulsion has evaporated, before or after step b).

15. The method of producing a combined carrier material composite material according to claim 14, wherein said carrier material comprises a net, a foam, a fibrous structure, a film, a gel, a silicone based adhesive or an acrylic adhesive, or any combinations thereof.

16. A method of producing a medical dressing comprising the steps of:
 a) producing a combined carrier material and composite material according to claim 14; and
 b) incorporating said combined carrier material and composite material into a medical dressing.

17. A method of producing a carrier material in the form of a gel comprising an oil-in-water emulsion for use as component in the medical dressing according to claim 12, comprising the steps of;
 a) providing an oil-in water emulsion comprising or consisting of oil droplets dispersed in an aqueous phase comprising one or more cellulose derivatives and nanocellulose; and
 b) contacting a gel with said oil-in-water emulsion.

18. A method of producing a medical dressing comprising the steps of:
 a) producing a gel comprising an oil-in water emulsion according to claim 17; and
 b) incorporating said gel comprising said oil-in-water emulsion into a medical dressing.

* * * * *